United States Patent
Wang et al.

(10) Patent No.: US 10,011,811 B2
(45) Date of Patent: Jul. 3, 2018

(54) CELL SEEDING DEVICE AND METHOD

(71) Applicant: Vericel Corporation, Cambridge, MA (US)

(72) Inventors: Yongzhong Wang, Melrose, MA (US);
Christopher Kelly, Charlton, MA (US);
Stephen Rapko, Franklin, MA (US);
Frank Quinno, Londonderry, NH (US);
Barbara Seymour, Netick, MA (US)

(73) Assignee: Vericel Corporation, Cambridge, MA (US)

( * ) Notice: Subject to any disclaimer, the term of this patent is extended or adjusted under 35 U.S.C. 154(b) by 0 days.

(21) Appl. No.: 14/088,999

(22) Filed: Nov. 25, 2013

(65) Prior Publication Data

US 2015/0147809 A1 May 28, 2015

(51) Int. Cl.
| | |
|---|---|
| *C12M 1/12* | (2006.01) |
| *C12M 3/00* | (2006.01) |
| *C12M 1/00* | (2006.01) |
| *C12M 1/36* | (2006.01) |
| *C12M 1/32* | (2006.01) |

(52) U.S. Cl.
CPC ............ *C12M 25/04* (2013.01); *C12M 23/20* (2013.01); *C12M 23/46* (2013.01); *C12M 25/14* (2013.01); *C12M 41/48* (2013.01); *C12M 23/12* (2013.01); *C12M 37/00* (2013.01)

(58) Field of Classification Search
CPC ...... C12M 25/04; C12M 23/12; C12M 23/20; C12M 25/14; C12M 37/00; C12M 41/48
USPC ...................................................... 435/309.1
See application file for complete search history.

(56) References Cited

U.S. PATENT DOCUMENTS

| | | | | |
|---|---|---|---|---|
| 3,846,241 A | * | 11/1974 | Faur | C12M 23/10 435/252.1 |
| 5,635,396 A | * | 6/1997 | Fedun | C12M 25/04 435/305.1 |
| 6,268,147 B1 | | 7/2001 | Beattie | |
| 2006/0172412 A1 | * | 8/2006 | Perrier | C12M 25/04 435/305.1 |
| 2007/0166819 A1 | * | 7/2007 | Ghosh | C12M 25/04 435/305.4 |
| 2013/0267019 A1 | | 10/2013 | Schmidt et al. | |

FOREIGN PATENT DOCUMENTS

| | | |
|---|---|---|
| EP | 0 773 286 A2 | 5/1997 |
| EP | 2390201 * | 11/2011 |
| GB | 1 360 949 | 7/1974 |

(Continued)

OTHER PUBLICATIONS

Geiss Gary K. et al. "Direct multiplexed measurement of gene expression with color-coded probe pairs" *Nature Biotechnology*, vol. 26, No. 3, Mar. 2008, pp. 317-325.

(Continued)

*Primary Examiner* — Michael L Hobbs
(74) *Attorney, Agent, or Firm* — Choate, Hall & Stewart LLP; Brenda Herschbach Jarrell; Robert N. Sahr

(57) ABSTRACT

Described is a device comprising an anchor, a tray including a well adapted to receive the anchor, and a cover adapted to engage the tray and cover the well. The device may be used to form a membrane-cell matrix having a substantially uniform distribution of the cells on the membrane in at least two dimensions.

22 Claims, 3 Drawing Sheets

(56) References Cited

FOREIGN PATENT DOCUMENTS

| WO | WO 03/003810 A | 1/2003 |
| WO | WO 2005/071401 A | 8/2005 |
| WO | WO 2012/081848 A2 | 6/2012 |
| WO | WO-2015/077240 A1 | 5/2015 |

OTHER PUBLICATIONS

International Search Report for PCT/US2014/066184 (Cell Seeding Device and Method, filed Nov. 18, 2014), issued by ISA/EPO, 4 pages dated Feb. 2, 2015.

Written Opinion for PCT/US2014/066184 (Cell Seeding Device and Method, filed Nov. 18, 2014), issued by ISA/EPO, 4 pages dated Feb. 2, 2015.

\* cited by examiner

CELL SEEDING DEVICE AND METHOD

BACKGROUND

When seeding cells on a surface of a membrane, several problems can arise. For example, cells can flow around edges of the membrane and become deposited on edges or an opposite surface of the membrane. Further, cells can settle on the surface in a non-uniform manner creating a cell layer without a uniform distribution. Still further, if the membrane is not fixed in place, the membrane can shift, twist, fold, etc. which can affect uniformity of the seeding.

Therefore, an improved device and method is needed to overcome the problems encountered when seeding cells on a membrane.

SUMMARY OF THE INVENTION

In an exemplary embodiment, a device according to the present invention comprises an anchor, a tray including a well adapted to receive the anchor, and a cover adapted to engage the tray and cover the well.

In an exemplary embodiment, the tray includes a top surface surrounding an opening of the well. The tray may include a flange disposed at least partially around a periphery of the top surface. The flange may include at least one first thread. The top surface may include a first rim formed at least partially around the periphery of the top surface.

In an exemplary embodiment, the well includes at least one first sidewall and a base. The at least one first sidewall may be disposed approximately perpendicular to the base. The base may include a second rim formed at least partially around a periphery of an external surface. The anchor may include at least one second sidewall enclosing a space. A first cross-sectional area of the base may be approximately equal to a second cross-sectional area of the space. The anchor may include at least one tab disposed on the at least one sidewall. The at least one tab may be disposed in a same plane as the at least one sidewall.

In an exemplary embodiment, the well is at least partially transparent and the anchor is at least partially colored.

In an exemplary embodiment, the cover includes a cavity adapted to receive the flange. The cavity may include at least one second thread adapted to engage the at least one first thread. The cavity may include a slot adapted to receive the first rim. The cover may include at least one rib formed on an outer surface.

In an exemplary embodiment, a device according to the present invention comprises an anchor including at least one first sidewall enclosing a space having X, Y, and Z dimensions, a tray including a well adapted to receive the anchor, the well having at least one second sidewall and a base having X and Y dimensions, and a cover adapted to engage the tray, wherein the X and Y dimensions of the space are approximately equal to the X and Y dimensions of the base such that when the anchor is in the well, at least one of the at least one first sidewall and at least one of the at least one second sidewall are in direct contact.

In an exemplary embodiment, a method of generating a membrane-cell matrix having a substantially uniform distribution of the cells on the membrane in at least two dimensions comprises providing a device comprising an anchor and a tray including a well adapted to receive the anchor, placing a membrane in the well, placing the anchor in the well at least partially in contact with the membrane, and filling the well at least partially with a medium containing cells. The method may further comprise removing the anchor from the well, and removing the membrane-cell matrix.

DETAILED DESCRIPTION

Exemplary embodiments of a cell seeding device according to the present invention may be used to seed cells on a membrane. For example, the cell seeding device may be utilized to achieve a uniform distribution of cells on a porous membrane. In an exemplary embodiment, a first uniform distribution is achieved on a first axis, a second uniform distribution is achieved on a second axis, and/or a third uniform distribution is achieved on a third axis.

In an exemplary embodiment, a cell seeding device according to the present invention comprises a tray having a well, an anchor adapted to fit within the well, and a cover adapted to engage the tray and cover the well.

Figure 1A:
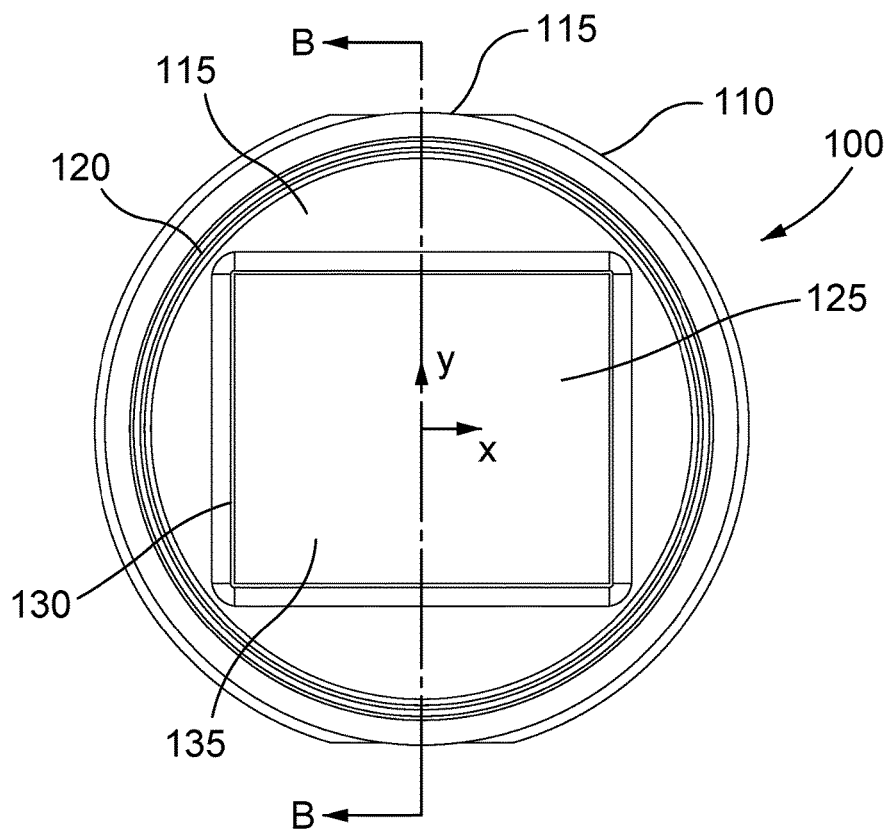
FIG. 1A shows an exemplary embodiment of a top view of a tray of a cell seeding device according to the present invention.
Figure 1B:
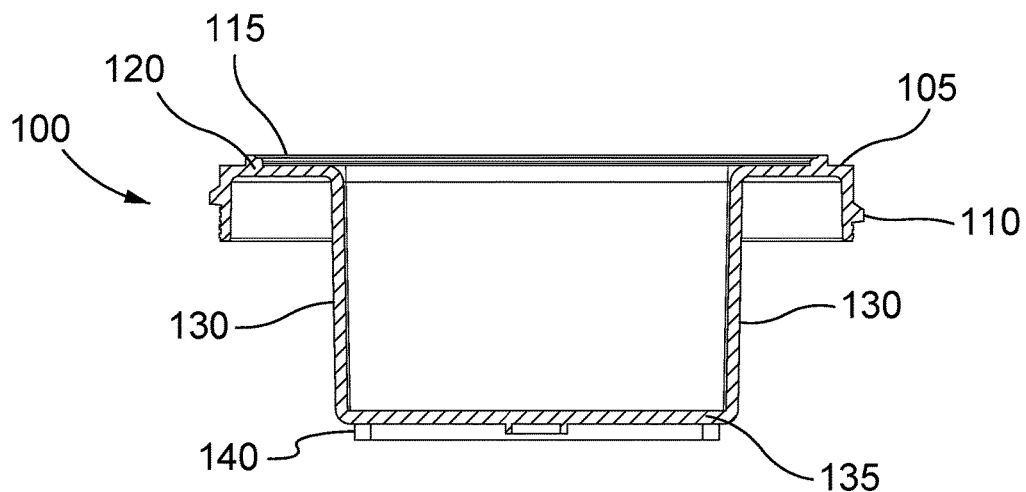
FIG. 1B shows an exemplary embodiment of a sectional view of a tray of a cell seeding device according to the present invention.

FIGS. 1A and 1B show an exemplary embodiment of a tray 100 of a cell seeding device according to the present invention. The tray 100 includes a flange 105 having at least one thread 110 formed at least partially on its periphery. In an exemplary embodiment, the flange 105 has a diameter of approximately 3.38 inches. The flange 105 is disposed around a top surface 115 of the tray 100. In an exemplary embodiment, the top surface 115 includes a first rim 120 formed at least partially on its periphery. The first rim 120 projects axially from the top surface 115. In an exemplary embodiment, the first rim 120 extends approximately 0.052 inches above the top surface 115.

In an exemplary embodiment, a well 125 is formed in the tray 100. In an exemplary embodiment, the well 125 includes a plurality of sidewalls 130 and a base 135. Each of the sidewalls 130 may include an upper portion coupled to the top surface 115 and a bottom portion coupled to the base 135. While the exemplary embodiment of the well 125 is described as having a plurality of sidewalls 130, those of skill in the art will understand that a circular or elliptical well may have a single sidewall. Further, those of skill in the art will understand that the well 125 may be any shape and include any number of sidewalls.

In an exemplary embodiment, the sidewalls 130 are approximately perpendicular to the top surface 115 and the base 135. In an exemplary embodiment, the base 135 is approximately 2 inches by approximately 1.612 inches, and the sidewalls 130 are approximately 1.28 inches from the base 135 to the top surface 115.

In an exemplary embodiment, a second rim 140 may be formed on an external surface of the base 135. The second rim 140 may provide for separation between the base 135 and a surface on which the tray 100 is placed and further provide support for the tray 100 to prevent tipping. In an exemplary embodiment, a frictional surface (e.g., rubber, bumps, etc.) may be formed on the second rim 140 to further enhance stability of the tray 100.

Figure 2A:
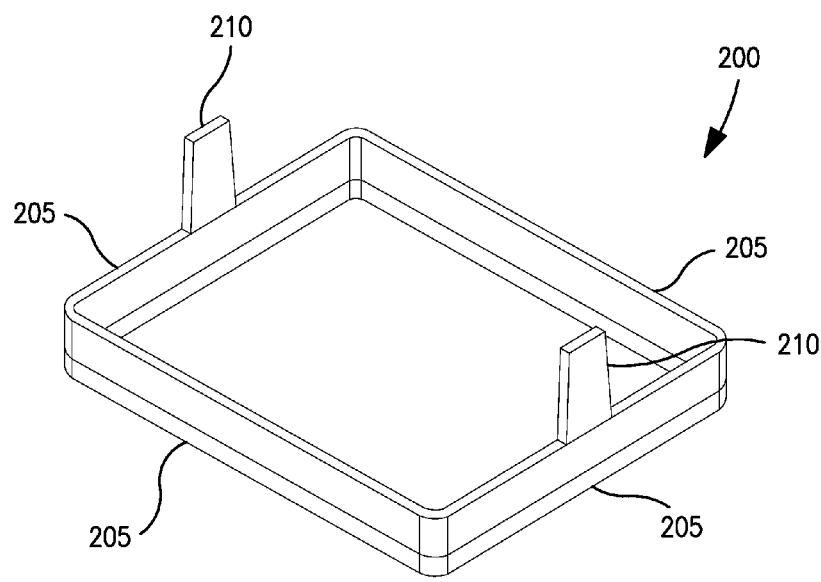
FIG. 2A shows an exemplary embodiment of a perspective view of an anchor for a cell seeding device according to the present invention.
Figure 2B:
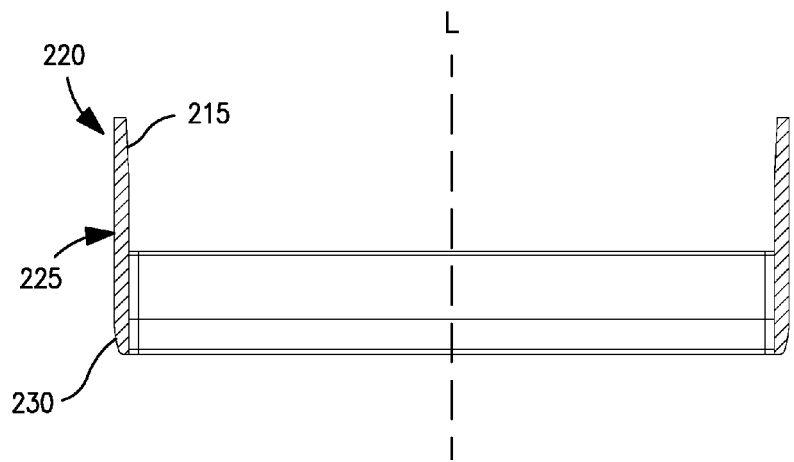
FIG. 2B shows an exemplary embodiment of a sectional view of an anchor for a cell seeding device according to the present invention.

FIGS. 2A and 2B show an exemplary embodiment of an anchor 200 for a cell seeding device according to the present invention. In an exemplary embodiment, the anchor 200 is adapted to be slidably disposed in the well 125. Thus, the anchor 200 is sized and shaped to fit within the well 125.

In an exemplary embodiment, the anchor 200 includes a plurality of sidewalls 205 and at least one tab 210 formed on a surface of at least one of the sidewalls 205. While the exemplary embodiment of the anchor 200 is described as having a plurality of sidewalls 205, those of skill in the art will understand that a circular or elliptical anchor may have a single sidewall. Further, those of skill in the art will understand that the anchor 200 may be any shape and size and include any number of sidewalls. In an exemplary embodiment, the sidewalls 205 enclose a space having a cross-sectional area (in the X-Y plane) which is equal to or less than a cross-sectional area (in the X-Y plane) of the base 135 of the well 125.

In an exemplary embodiment, the at least one tab 210 is disposed approximately in-plane with the sidewall 205 and extends above an upper surface of the sidewall 205 a predetermined distance. In an exemplary embodiment, the predetermined distance is 0.4 inches. In an exemplary embodiment, the tab 210 has a frusto-conical shape having a broad portion coupled to the sidewall 205 and a narrowed portion displaced from the sidewall 205. Those of skill in the art will understand that the tab 210 may be any shape or size and disposed at any angle relative to the sidewall 205. In an exemplary embodiment, the predetermined distance is determined such that a portion of the tab 210 extends above the top surface 115 but does not extend above the first rim 120.

As shown in FIG. 2B, in an exemplary embodiment, the sidewall 205 has an inner surface 215 which is approximately parallel to a longitudinal axis L of the device. The sidewall 205 further includes an outer surface 220 having an upper portion 225 and a lower portion 230 which, in use, is adapted to engage a membrane in the well 125. The upper portion 225 is approximately parallel to the longitudinal axis L of the device, and the lower portion 230 is disposed at a non-parallel angle to the upper portion 225. In an exemplary embodiment, the lower portion 230 is angled radially toward the longitudinal axis L of the device. For example, the angle of the lower portion 230 leaves a space for a periphery of the membrane which extends beyond a periphery of the lower portion 230. In an exemplary embodiment, an angle of the lower portion 230 relative to the upper portion 225 is approximately 10.3°.

In an exemplary embodiment, a first set of sidewalls 205 is approximately 1.99 inches long and a second set of sidewalls 205 is approximately 1.6 inches long.

In an exemplary embodiment, the well 125 may be formed from a first material which is substantially transparent, and the anchor 200 may be formed from a second material which has a color visible through the first material of the well 125. For example, it may be beneficial if the anchor 200 is red so that a user of the device can ensure that the anchor 200 is properly situated within the well 125 and/or makes the anchor 200 easier to remove from the well 125.

Figure 3C:
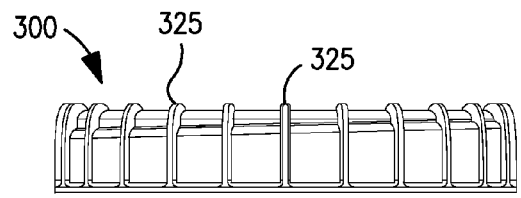
FIG. 3C shows an exemplary embodiment of a side view of a cover of a cell seeding device according to the present invention.
Figure 3A:
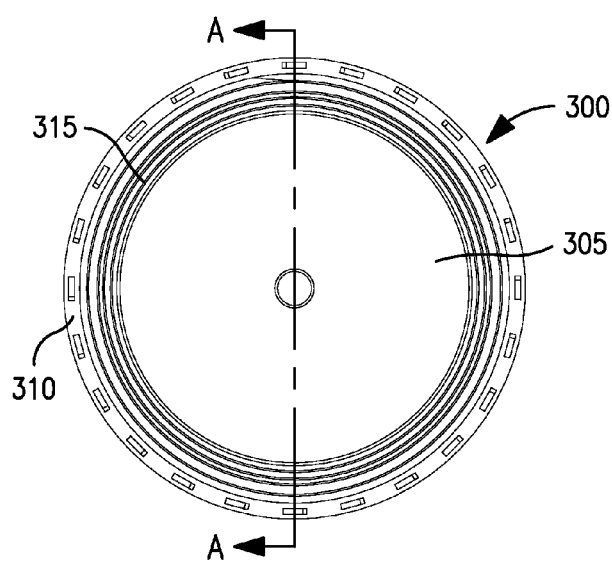
FIG. 3A shows an exemplary embodiment of a bottom view of a cover of a cell seeding device according to the present invention.
Figure 3B:
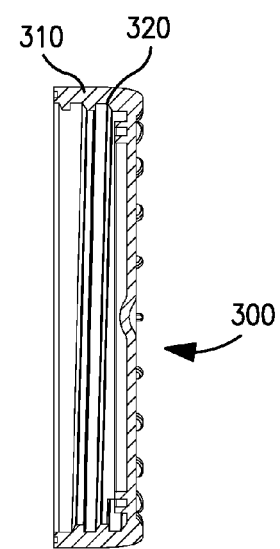
FIG. 3B shows an exemplary embodiment of a sectional view (along section A-A in FIG. 3A) of a cover of a cell seeding device according to the present invention.

FIGS. 3A-C show an exemplary embodiment of a cover 300 of a cell seeding device according to the present invention. The cover 300 includes a cavity 305 adapted to receive the flange 105 and the top surface 115 of the tray 100. The cavity 305 includes an interior surface including a slot 315 adapted to at least partially engage the first rim 120. The engagement of the slot 315 and the first rim 120 may facilitate alignment of the cover 300 and the tray 100 when being coupled together. In an exemplary embodiment, the slot 315 may be annular or any other shape or size to correspond to the shape and size of the first rim 120.

The cavity 305 may further include a sidewall 310 having a thread 320 formed on an interior surface which is adapted to engage the thread 110 on the tray 100. Thus, rotation of the cover 300 relative to the tray 100 causes engagement (or disengagement) via the threads 110, 320. While the exemplary embodiments of the invention are described as utilizing the threads 110, 320 to engage the cover 300 and the tray 100, those of skill in the art will understand that any other engagement mechanism (e.g., friction, snap-fit, clips, hooks, etc.) may be utilized to ensure that the cover 300 properly engages and disengages the tray 100.

An outer surface of the cover 300 (shown in FIG. 3C) may include one or more ribs 325. The ribs 325 provide an abutment surface for a user's fingers when handling the cover 300. For example, when rotating the cover 300 relative to the tray 100, the ribs 325 provide a surface to which the user can apply varying degrees of force to effect the rotation and engagement or disengagement of the cover 300 from the tray 100. While the exemplary embodiment of the cover 300 is described as having ribs 325, those of skill in the art will understand that the at least one rib 325 may be formed on the tray 100 (in addition to, or instead of the cover 300), and that any other element (e.g., recesses, projections, handles, frictional surfaces, etc.) or combination of elements may be utilized.

In an exemplary embodiment, the anchor 200 may be formed integrally with the cover 300. In this exemplary embodiment, one or more stem elements (not shown) may extend from the inner surface of the cavity 305 to the tab 210 and/or the sidewall 205.

In an exemplary embodiment, the device may be utilized to seed cells on a membrane. For example, the device may be used to seed cells for a matrix-induced autologous chondrocyte implantation (MACI®) implant. In another example, the device may be used to seed a sponge matrix.

If the cover 300 is coupled to the tray 100, the cover 300 is removed from the tray 100. A membrane is then placed in the well 125 on or adjacent to the base 135. The membrane may have dimensions (in the X and Y planes) equal to or less than the dimensions of the base 135, and thus may be pre-fabricated or pre-cut to fit within the well 125 on the base 135. The membrane may be smoothed (e.g., using forceps) to remove any air bubbles between the base 135 and the membrane. The anchor 200 is then placed in the well 125 and on top of the membrane. In an exemplary embodiment, the anchor 200 may be held by the tab 210 with fingers or forceps.

In an exemplary embodiment, cells are then placed into the well 125. For example, the cells may be mixed into a medium, e.g., Dulbecco's modified Eagle's medium (DMEM), and poured into the well 125. In an exemplary embodiment, there is limited, if any, space between the sidewalls 205 of the anchor 200 and the sidewalls 130 of the well 125. Thus, most, if not all, of the mixture is confined within the sidewalls 205 of the anchor 200 and the membrane. For example, in an exemplary embodiment in which the well 125 includes four sidewalls 130 and the anchor 200 includes four sidewalls 205, at least two of the sidewalls 130, 205 (parallel or perpendicular) are in direct contact while the anchor 200 is in the well 125. Confining the mixture in this manner promotes uniform cell distribution over the membrane in the X-Y plane and preferably the Z-plane. The cover 300 may then be coupled to the tray 100, and the device may be left undisturbed for a predetermined period of time (e.g., 2-3 days).

After the predetermined period of time, the cover 300 is removed from the tray 100, and the anchor 200 is removed from the well 125. For example, the user may engage the anchor 200, e.g., via the tab 210, using fingers or forceps. When the anchor 200 is removed, the membrane-cell matrix may be removed.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A device comprising: an anchor comprising at least one sidewall comprising an upper portion that is disposed in a plane approximately parallel to the longitudinal axis (L) of the device and a lower portion with an outer surface of the lower portion angled radially toward the longitudinal axis (L) of the device wherein when a membrane is present, the lower portion engages at least a portion of the membrane: and at least one tab disposed on the upper portion of at least one sidewall, wherein the at least one tab is disposed in the same plane as the upper portion on which it is disposed; a tray including a well adapted to receive the anchor, wherein the anchor is adapted to be slidably disposed in the well; and a cover adapted to engage the tray and cover the well.

2. The device according to claim 1, wherein the tray includes a top surface surrounding an opening of the well.

3. The device according to claim 2, wherein the tray includes a flange disposed at least partially around a periphery of the top surface.

4. The device according to claim 3, wherein the flange includes at least one first thread.

5. The device according to claim 4, wherein the top surface includes a first rim formed at least partially around the periphery of the top surface.

6. The device according to claim 5, wherein the cover includes a cavity adapted to receive the flange.

7. The device according to claim 6, wherein the cavity includes at least one second thread adapted to engage the at least one first thread.

8. The device according to claim 6, wherein the cavity includes a slot adapted to receive the first rim.

9. The device of claim 1, wherein the well includes at least one first sidewall and a base.

10. The device according to claim 9, wherein the base includes a second rim formed at least partially around a periphery of an external surface.

11. The device according to claim 9, wherein a first cross-sectional area of the base is approximately equal to a second cross-sectional area of the space.

12. The device according to claim 1, wherein the anchor includes a second sidewall enclosing a space.

13. The device according to claim 12, wherein the cover includes at least one rib formed on an outer surface.

14. The device according to claim 1, wherein the well is at least partially transparent and the anchor is at least partially colored.

15. The device of claim 1, further comprising a membrane, wherein the membrane is in the well or adjacent to a base of the well.

16. The device of claim 15, wherein the membrane comprises a substantially uniform distribution of cells.

17. The device of claim 1, further comprising a membrane, wherein the anchor is on top of the membrane.

18. The device of claim 17, wherein the membrane comprises a substantially uniform distribution of cells.

19. The device of claim 1, further comprising a membrane, wherein the membrane is in the well or adjacent to a base of the well and wherein the anchor is on top of the membrane such that a mixture comprising cells is confined within a volume bounded by the sidewalls of the anchor and the membrane.

20. The device of claim 19, wherein confining the mixture comprising cells promotes uniform cell distribution over the membrane.

21. A method of generating a membrane-cell matrix having a substantially uniform distribution of the cells on the membrane in at least two dimensions comprising:
providing the device of claim 1;
placing a membrane in the well;
placing the anchor in the well at least partially in contact with the membrane;
and filling the well at least partially with a medium containing cells.

22. The method according to claim 21, further comprising: removing the anchor from the well; and removing the membrane-cell matrix.

* * * * *

UNITED STATES PATENT AND TRADEMARK OFFICE
CERTIFICATE OF CORRECTION

PATENT NO. : 10,011,811 B2
APPLICATION NO. : 14/088999
DATED : July 3, 2018
INVENTOR(S) : Yongzhong Wang et al.

It is certified that error appears in the above-identified patent and that said Letters Patent is hereby corrected as shown below:

On the Title Page

In the Inventors item (72), for Inventor Barbara Seymour, please delete "Netick, MA (US)" and insert -- Natick, MA (US) --

In the Claims

Column 5, Claim 1, Line 33, please delete "membrane:" and insert -- membrane; --

Signed and Sealed this
Second Day of October, 2018

Andrei Iancu
*Director of the United States Patent and Trademark Office*